US00PP20643P2

(12) United States Plant Patent
Stever

(10) Patent No.: US PP20,643 P2
(45) Date of Patent: Jan. 12, 2010

(54) ***CHASMANTHIUM* PLANT NAMED 'RIVER MIST'**

(50) Latin Name: *Chasmanthium latifolium*
Varietal Denomination: River Mist

(75) Inventor: Karen R. Stever, Gainesville, GA (US)

(73) Assignee: ITSaul Plants, LLC, Alpharetta, GA (US)

( * ) Notice: Subject to any disclaimer, the term of this patent is extended or adjusted under 35 U.S.C. 154(b) by 0 days.

(21) Appl. No.: 12/288,809

(22) Filed: Oct. 23, 2008

(51) Int. Cl.
*A01H 5/00* (2006.01)

(52) U.S. Cl. ..... Plt./384

(58) Field of Classification Search ..... Plt./384
See application file for complete search history.

*Primary Examiner*—June Hwu
(74) *Attorney, Agent, or Firm*—Penny J. Aguirre

(57) ABSTRACT

A new cultivar of *Chasmanthium latifolium*, 'River Mist', characterized by its green and white variegated foliage and its white seed heads that cascade from upright culms.

2 Drawing Sheets

Botanical classification: *Chasmanthium latifolium.*

Varietal designation: 'River Mist'.

BACKGROUND OF THE INVENTION

The present invention relates to a new and distinct cultivar of *Chasmanthium latifolium* and will be referred to hereafter by its cultivar name, 'River Mist'. 'River Mist' represents a new cultivar of Northern sea oats, an ornamental grass grown for landscape use.

The Inventor discovered the new cultivar, 'River Mist', as a naturally whole plant mutation in July 2004. 'River Mist' was selected as a single unique plant amongst 500 seedlings of an unnamed and unpatented plant of *Chasmanthium latifolium* that were growing in one-gallon containers in a nursery in Alpharetta, Ga.

Asexual reproduction of the new cultivar was first accomplished by the Inventor by culm division in Alpharetta, Ga. in July of 2004. Propagation by culm division and in vitro propagation have determined that the characteristics of this cultivar are stable and reproduce true to type in successive generations.

SUMMARY OF THE INVENTION

The following traits have been repeatedly observed and represent the characteristics of the new cultivar, 'River Mist'. These attributes in combination distinguish 'River Mist' from any selections of *Chasmanthium* known to the Inventor.

1. 'River Mist' exhibits foliage that is variegated with vertical stripes of white and green.
2. 'River Mist' exhibits white seed heads that cascade from upright culms.

The parent plant, *Chasmanthium latifolium*, differs from 'River Mist' in having solid green, non-variegated foliage, wider leaves and green seed heads. There are no other cultivars of *Chasmanthium latifolium* with variegated foliage known to the Inventor.

BRIEF DESCRIPTION OF THE DRAWING

The accompanying colored photographs illustrate the overall appearance and distinct characteristics of two year-old plants the new *Chasmanthium* as grown in a garden in Alpharetta, Ga.

The photograph in FIG. 1 illustrates the overall habit and appearance of 'River Mist'.

Figure 1:
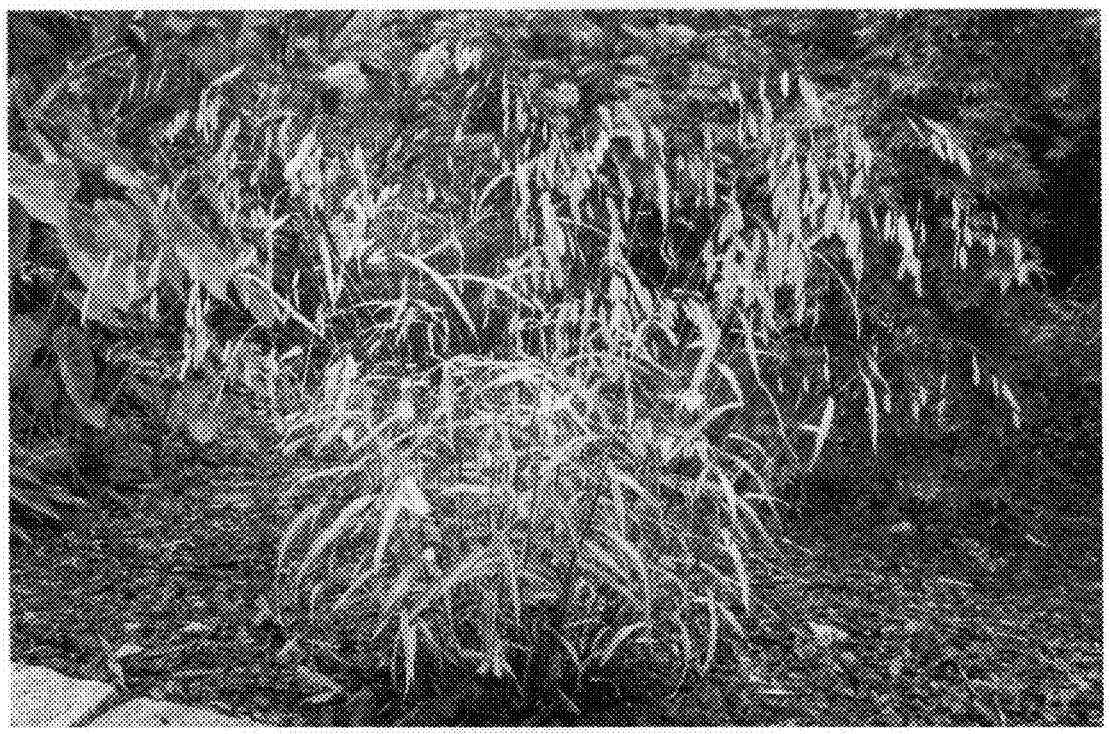
Figure 2:
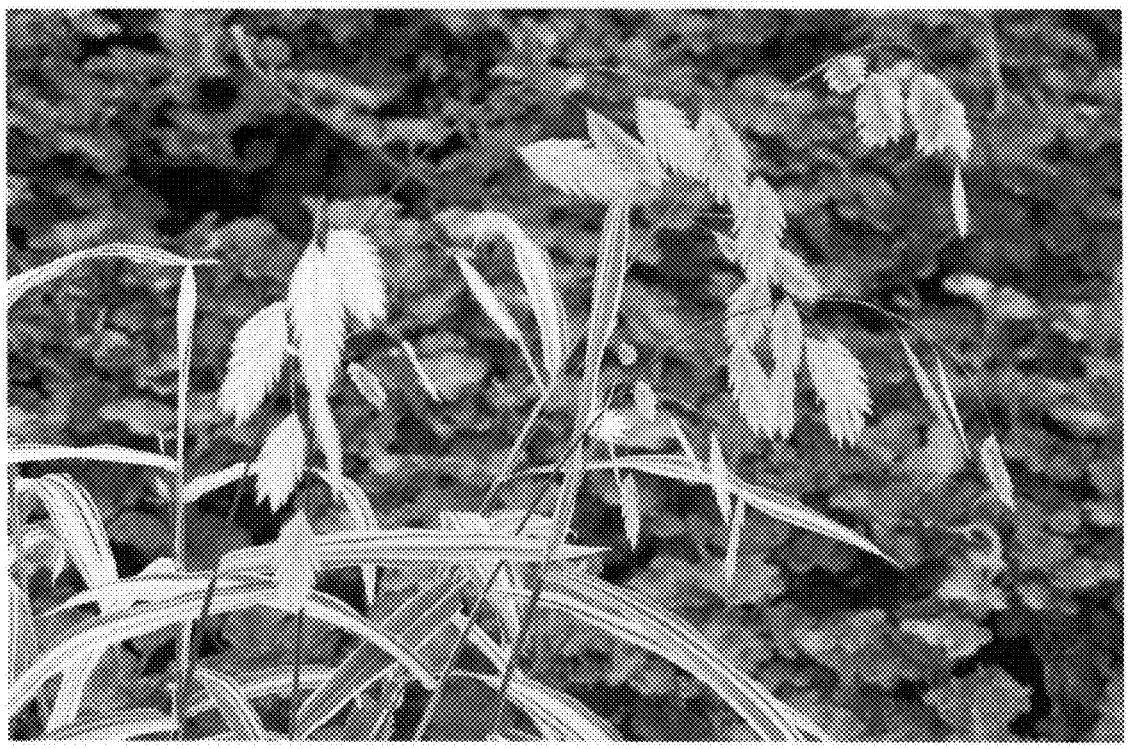

The photograph in FIG. 2 provides is a close-up view of the foliage and seed heads of 'River Mist'.

The colors in the photographs are as close as possible with the photographic and printing technology utilized. The colors in the photograph may differ slightly from the color values cited in the detailed botanical description, which accurately describe the colors of the new *Chasmanthium.*

DETAILED BOTANICAL DESCRIPTION

The following is a detailed description of two year-old plants of the new cultivar as grown outdoors in a one-gallon container in Alpharetta, Ga. 'River Mist' has not been observed under all possible environmental conditions. The phenotype may vary somewhat with variations in temperature, day-length, light intensity, soil types, and water and fertility levels without, however, any variance in genotype. The color determination is in accordance with the 2007 R.H.S. Colour Chart of The Royal Horticultural Society, London, England, except where general color terms of ordinary dictionary significance are used.

General description:

*Blooming period.*—Inflorescences (seed heads) emerge in late summer and persist into winter in Georgia.

*Plant habit.*—Herbaceous, clump-forming, ornamental grass with sturdy upright culms with cascading racemes of nodding spikelets when grown in full sun with a more lax habit when grown in shady conditions.

*Height and spread.*—Reaches about 46 cm in height with a spread of about 30 cm in a one-gallon container and matures in the garden to about 76 cm (30 inches) in height and spread.

*Hardiness.*—U.S.D.A. Zones 4 to 9.

*Diseases and pests.*—No susceptibility or resistance to diseases or pests has been observed.

*Root description.*—Deep rooted with fibrous roots from short rhizomes.

*Rhizome color.*—155D with diagonal ridges of 177D.

Growth and propagation:

*Propagation.*—Culm division or tissue culture (preferred).

*Time required for root development.*—Roots initiate about 2 weeks in stage 3 rooting solution with roots well developed in 3 to 4 weeks, rooted plantlets develop in a 72-cell plug in about 5 weeks.

*Growth rate.*—Moderate.

Culm (stem) description:

*General.*—Oval in shape, pithy.

*Culm aspect.*—Rigid and held erect in full sun.

*Branching.*—Average of 2 branches with main stems emerging from crown and lateral branches originating near base.

*Culm color* (*sheathed*).—New growth; 138A to 146A and with stripes of NN155A, mature;146A with some stripes of NN155A.

*Culm size.*—Average of 3 mm in width and 32 cm in height to base of inflorescence, lateral branches; an average of 2.4 mm in width and 11 cm in length.

*Culm surface.*—Glabrous.

*Internode length.*—Average of 2.5 cm (between leaf blade attachments).

*Ligule.*—Membranous towards center and pubescent near edges, an average of 3 mm in with and 1 mm in depth, 144D in color and slightly suffused with N79C. and sparsely covered with, very fine whitish hairs about 3 mm in length.

Foliage description:

*Leaf arrangement.*—Alternate, 2 ranked.

*Leaf shape.*—Lanceolate.

*Leaf division.*—Simple.

*Leaf base.*—Sheathed to next distal node, sheath surrounds entire culm.

*Leaf apex.*—Attenuating to a fine tip.

*Leaf aspect.*—Leaf blades diverge from leaf sheath at about a 45° to 80° angle from center of culm.

*Leaf venation.*—Parallel, not conspicuous, coloration matches leaf color.

*Leaf margins.*—Entire, slightly scabrous.

*Leaf auricles.*—Not present.

*Leaf persistence.*—Foliage dries but is persistent throughout the winter.

*Leaf attachment.*—Sheathed.

*Leaf bud arrangement.*—Curled.

*Leaf size.*—Obtains about 13 cm in length and an average of 1.2 cm at widest point.

*Leaf surface.*—Glabrous on upper surface and lower surface.

*Leaf number.*—Average of 8 per stem 32 cm in length.

*Leaf color.*—Variegated, new foliage upper and lower surfaces; longitudinal stripes of NN155A and 144A, mature foliage upper and lower surfaces; longitudinal stripes of NN155A and 137D and 138B.

*Leaf fragrance.*—None.

*Peduncle description.*—Average of 6 cm in length and 0.7 mm in width, 137A in color.

Inflorescence description (seed heads):

*General description.*—Racemes of alternating spikelets on thin wiry pedicels borne above the foliage at terminus of culms and lateral branches.

*Lastingness of inflorescence.*—Seed heads are persistent into winter.

*Fragrance.*—None.

*Raceme number.*—Average of 3 per culm and branch, emerge in succession.

*Raceme aspect.*—Held upright when they emerge and then gently cascade when mature.

*Raceme size.*—About 14 cm in length and 5 mm in width.

*Spikelets.*—Average of 1.5 cm in length and 4 mm in width, lanceolate to elliptical in shape and flattened, average of 7 per rachilla, comprised of an average of 6 laterally compressed florets, color emerges 149D to 144D and mature to 155C and turn to 191D in fall.

*Rachilla.*—Average of 12 cm in length and 0.7 mm in width, 137A in color, glabrous surface, internode length of spikelets about 2 cm.

*Pedicels.*—Average of 1.4 cm in length and 0.3 mm in width, wiry, 137A in color, glabrous surface.

*Reproductive organs.*—The species is bisexual, however no reproduction organs could be readily observed.

*Seed.*—Caryopsis, about 3 mm in length and 2 mm in width, 155D in color.

It is claimed:

1. A new and distinct cultivar of *Chasmanthium* plant named 'River Mist' as herein illustrated and described.

* * * * *